United States Patent
Haider

(10) Patent No.: US 9,136,028 B2
(45) Date of Patent: Sep. 15, 2015

(54) ROTATABLE CONTOUR COLLIMATOR HAVING A LIQUID IMPERMEABLE TO X-RAYS

(71) Applicant: Sultan Haider, Erlangen (DE)

(72) Inventor: Sultan Haider, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 364 days.

(21) Appl. No.: 13/691,297

(22) Filed: Nov. 30, 2012

(65) Prior Publication Data

US 2013/0142313 A1    Jun. 6, 2013

(30) Foreign Application Priority Data

Dec. 1, 2011 (DE) .................... 10 2011 087 590

(51) Int. Cl.
*G21K 1/04* (2006.01)
*G21K 1/02* (2006.01)

(52) U.S. Cl.
CPC . *G21K 1/02* (2013.01); *G21K 1/046* (2013.01)

(58) Field of Classification Search
CPC ............................. G21K 1/04; G21K 1/046
USPC ........................................................ 378/150
See application file for complete search history.

(56) References Cited

U.S. PATENT DOCUMENTS

| | | | |
|---|---|---|---|
| 4,438,991 A | 3/1984 | Lundgren | |
| 4,794,629 A | 12/1988 | Pastyr et al. | |
| 4,856,042 A * | 8/1989 | Staron et al. | 378/147 |
| 5,037,374 A | 8/1991 | Carol | |
| 5,299,249 A * | 3/1994 | Burke et al. | 378/15 |
| 5,442,675 A | 8/1995 | Swerdloff et al. | |
| 5,596,619 A * | 1/1997 | Carol | 378/65 |
| 5,745,279 A | 4/1998 | Ciscato et al. | |
| 5,889,834 A | 3/1999 | Vilsmeier et al. | |
| 6,052,436 A | 4/2000 | Huttner et al. | |
| 6,118,855 A | 9/2000 | Welters et al. | |
| 6,188,749 B1 | 2/2001 | Schiller et al. | |
| 6,757,355 B1 | 6/2004 | Siochi | |
| 6,813,336 B1 | 11/2004 | Siochi | |
| 7,015,490 B2 | 3/2006 | Wang et al. | |
| 7,180,980 B2 | 2/2007 | Nguyen | |
| 7,386,099 B1 | 6/2008 | Kasper et al. | |
| 7,894,574 B1 | 2/2011 | Nord et al. | |
| 7,993,058 B2 | 8/2011 | Bohn et al. | |
| 2003/0202632 A1 | 10/2003 | Svatos et al. | |
| 2005/0058245 A1 | 3/2005 | Ein-Gal | |
| 2009/0010395 A1 | 1/2009 | Ein-Gal | |
| 2009/0041199 A1 | 2/2009 | Bohn | |
| 2011/0115686 A1 * | 5/2011 | Hauhe et al. | 343/841 |

FOREIGN PATENT DOCUMENTS

DE    10 2006 039 793 B3    1/2008

OTHER PUBLICATIONS

German Office Action dated Jul. 30, 2012 for corresponding German Patent Application No. DE 10 2011 087 590.5 with English translation.

* cited by examiner

*Primary Examiner* — Brooke Purinton
(74) *Attorney, Agent, or Firm* — Lempia Summerfield Katz LLC

(57) ABSTRACT

A contour collimator and a method for setting a contour of a radiation path of an x-ray are provided. A liquid impermeable to the x-ray forms the contour.

19 Claims, 3 Drawing Sheets

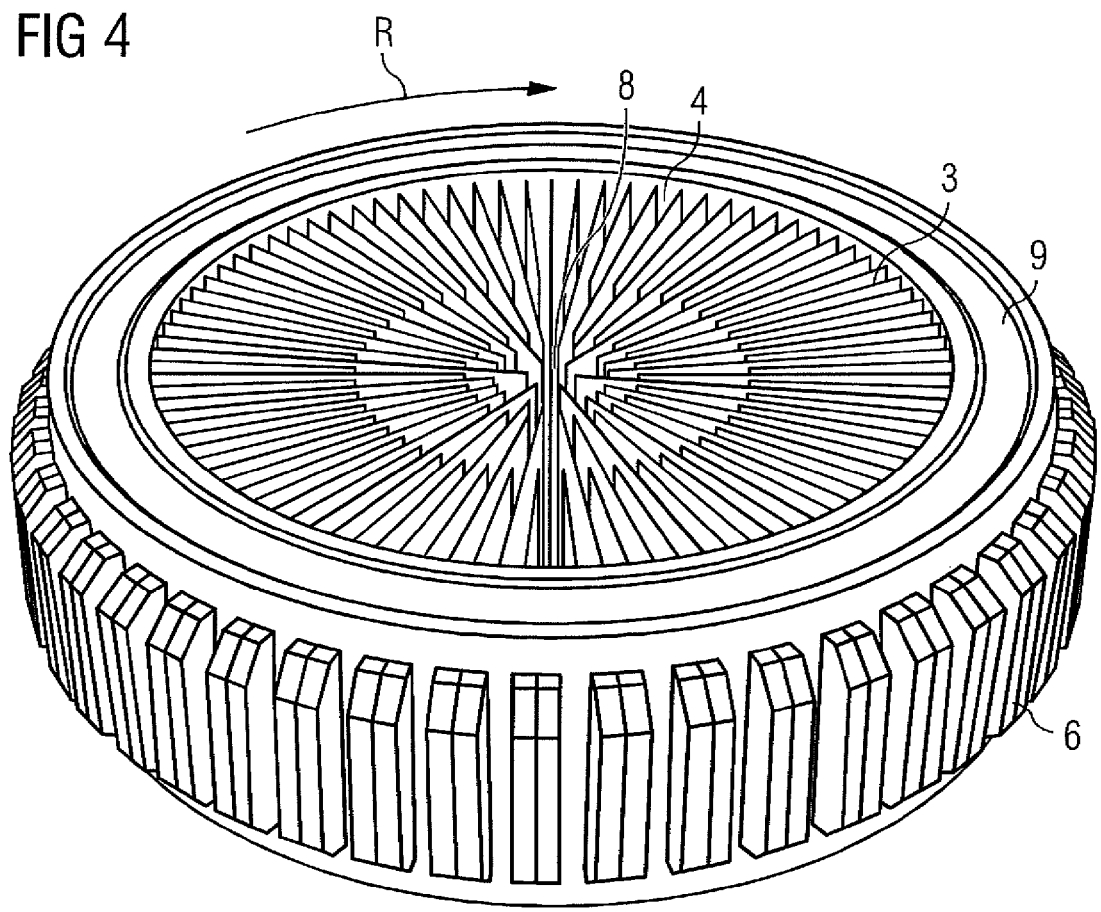

ROTATABLE CONTOUR COLLIMATOR HAVING A LIQUID IMPERMEABLE TO X-RAYS

This application claims the benefit of DE 10 2011 087 590.5, filed on Dec. 1, 2011, which is hereby incorporated by reference.

BACKGROUND

The present embodiments relate to a contour collimator and an associated method for radiation therapy.

A contour collimator is used in radiation therapy to treat tumors. In radiation therapy, a tumor is irradiated with energy-rich radiation (e.g., using high-energy x-rays from a linear accelerator). In the process, the contour collimator is introduced into the radiation path of the x-rays. The contour collimator has a radiation-permeable opening, the contour of which is to correspond to the contour of the tumor. The contour therefore forms an aperture to allow the x-rays to pass. Only the tumor and not the surrounding healthy body tissue is irradiated with x-rays. The contour collimator allows almost any arbitrary contour of a tumor to be reproduced.

Many collimators for radiation therapy are multi-leaf collimators such as are described, for example, in the application DE 10 2006 039793 B3. The multi-leaf collimator includes a number of leaves (e.g., 160 leaves) that may be moved in a motor-driven manner counter to one another in order to form the opening. The leaves include a material absorbing the x-ray radiation. In generic terms, two leaf packages are arranged opposite one another such that the two leaf packages may be moved with front faces towards or away from one another.

Each of the leaves may be moved separately by an electric motor. Since during the positioning of the leaves slight deviations may occur between a target specification and the actual position of the leaves set, each leaf has a position measuring device, with which the actually set position may be determined precisely.

The unexamined patent application US 2009/0 010 395 A1 discloses a contour collimator having a liquid impermeable to x-rays that is arranged in a container. The shape of the contour forms a contour bounding the radiation path.

The patents U.S. Pat. No. 6,188,749 B1 and U.S. Pat. No. 6,118,855 A disclose contour collimators with liquids.

SUMMARY AND DESCRIPTION

The present embodiments may obviate one or more of the drawbacks or limitations in the related art. For example, a contour collimator that may be used instead of a multi-leaf collimator and may reproduce a contour in a robust and rapid manner is provided.

A contour collimator for setting a contour of a radiation path of an x-ray is provided. The contour forms an aperture (e.g., an opening in the contour collimator). Aperture refers to a free opening or a diameter, through which x-rays may be sent or received. The contour collimator includes a liquid impermeable to x-rays that forms the contour. The present embodiments afford the advantage of a collimator that is simple and robust to operate in order to form a contour for x-rays.

In one embodiment, the liquid may rotate at right angles to the radiation path. As a result, a centripetal force acts on the liquid.

In one embodiment, the contour collimator includes leaves that are arranged radially around an axis of rotation. First end points in a direction of the axis of rotation and tapered chambers are formed between the leaves. The tapered chambers are filled at least partially with liquid. This is advantageous in that the resolution of the contour may be changed in accordance with the number of chambers.

The axis of rotation may lie in parallel with the radiation path of the x-rays.

In another embodiment, the contour collimator includes pump units that exert pump forces on the liquid in the direction of the centripetal force acting on the liquid. As a result, the contour is formed.

In one development, each individual pump unit may supply another chamber.

The liquid advantageously includes an eutectic alloy containing gallium, indium and tin (e.g., the alloy with the product name Galinstan®).

A method for setting a contour of a radiation path of x-rays with a contour collimator is also provided. The contour and thus also an aperture is formed by liquid impermeable to x-rays.

In one embodiment of the method, the liquid may rotate about an axis of rotation parallel to the radiation path.

The liquid may also be pumped in the direction of the centripetal force acting on the liquid, where the contour is formed.

BRIEF DESCRIPTION OF THE DRAWINGS

FIG. 4 shows a spatial view of one embodiment of a contour collimator.

DETAILED DESCRIPTION OF THE DRAWINGS

Figure 1:
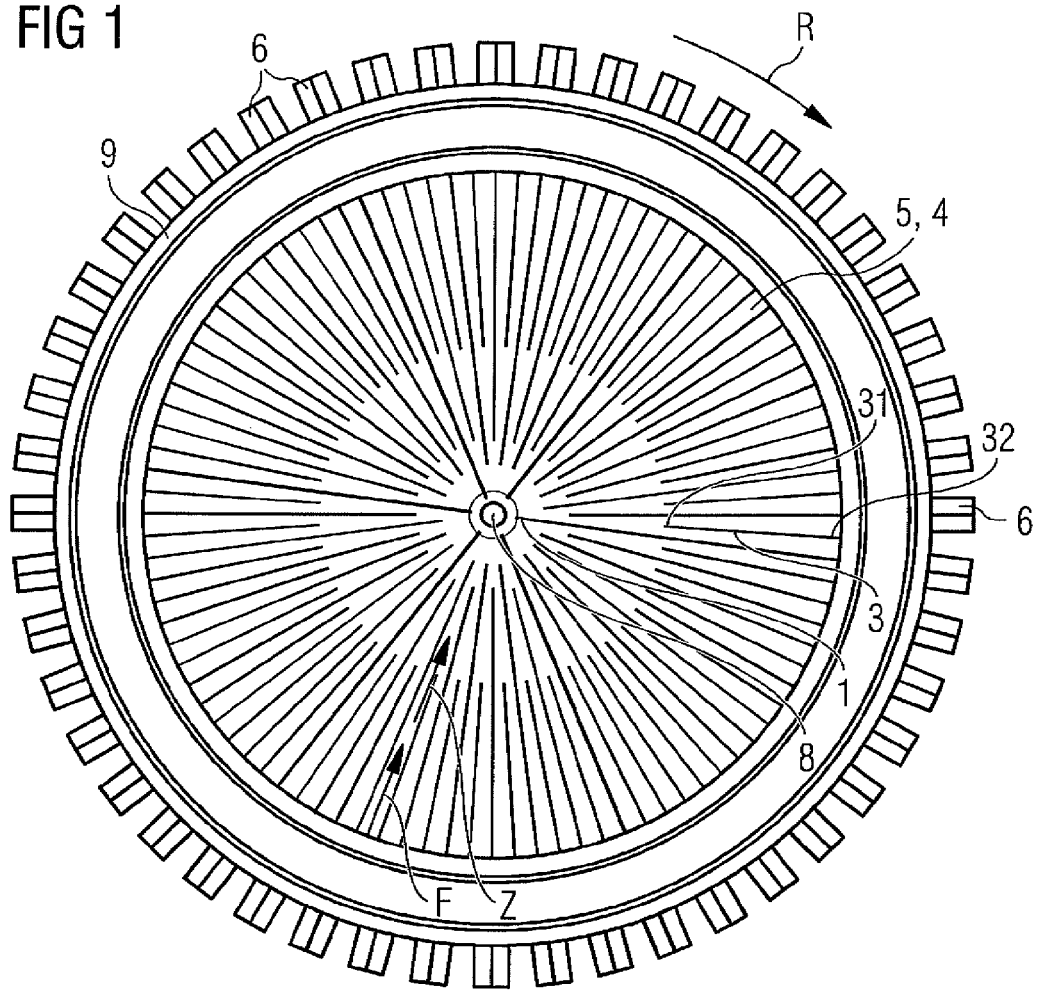
FIG. 1 shows a top view of one embodiment of a contour collimator.

One embodiment of a contour collimator shown in FIG. 1 includes a cylindrical housing 9, in which leaves 3 are arranged in a radial manner. First ends 31 of the leaves 3 point in a direction of an axis of rotation 8 of the contour collimator. Second ends 32 of the leaves 3 point outwards. The leaves 3, together with the housing 9, form tapered chambers 5 that are filled with a liquid 4 impermeable to x-rays.

The height of the leaves 3 is selected such that, as with conventional multi-leaf collimators, only parallel x-rays reach the target volume as far as possible, and an adequate shielding of the radiation is also provided.

Rotation of the contour collimator around the axis of rotation 8 in a direction of rotation R produces the centripetal force Z on the liquid 4. The centripetal force Z holds the liquid 4 on a circular path around the axis of rotation 8. With the aid of pump units 6 arranged on the periphery of the housing 9, liquid 4 may be pushed or pumped out of a storage container 7 of the housing 9 into the chambers 5. With the aid of the pump units 6, liquid 4 is transported in the direction of the axis of rotation 8 counter to the centrifugal force, shown by a pump force F. Depending on the pump pressure, the "fill level" in each chamber 5 may be different, so that the liquid 4 forms a contour 1.

FIG. 1 shows the contour 1 embodied in a circular manner. A temporal change in the pump force F provides that despite rotation of the contour collimator, rotation-symmetrical contours may also not be generated. A rotation frequency of the contour collimator may amount to a couple of hundred Hertz.

An euctectic alloy made of gallium, indium and tin that is available under the market name Galinstan® may be used as the liquid. Galinstan® is liquid at room temperature and, according to manufacturer instructions, passes into the solid aggregate state at temperatures below −19 degrees Celsius. Similarly to quicksilver, Galinstan® has the tendency to amalgamate with solid metals (e.g., aluminum or copper may dissolve with Galinstan).

Figure 2:
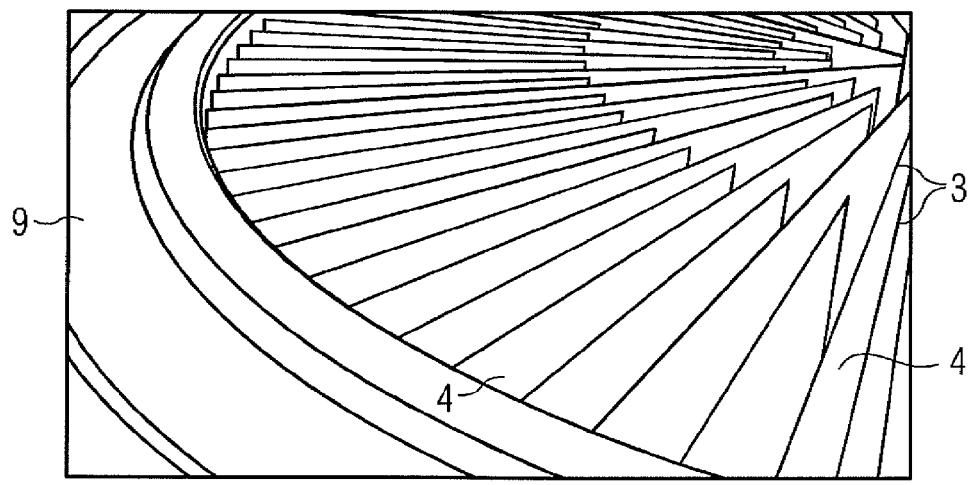
FIG. 2 shows a spatial partial view of one embodiment of a contour collimator.

FIG. 2 shows a partial view of one embodiment of a contour collimator in a perspective representation. The leaves 3 are arranged radially in the housing 9. The leaves 3 form chambers 4 that may be filled with a liquid impermeable to x-rays. The resolution of the contour may be improved by different lengths of the leaves.

Figure 3:
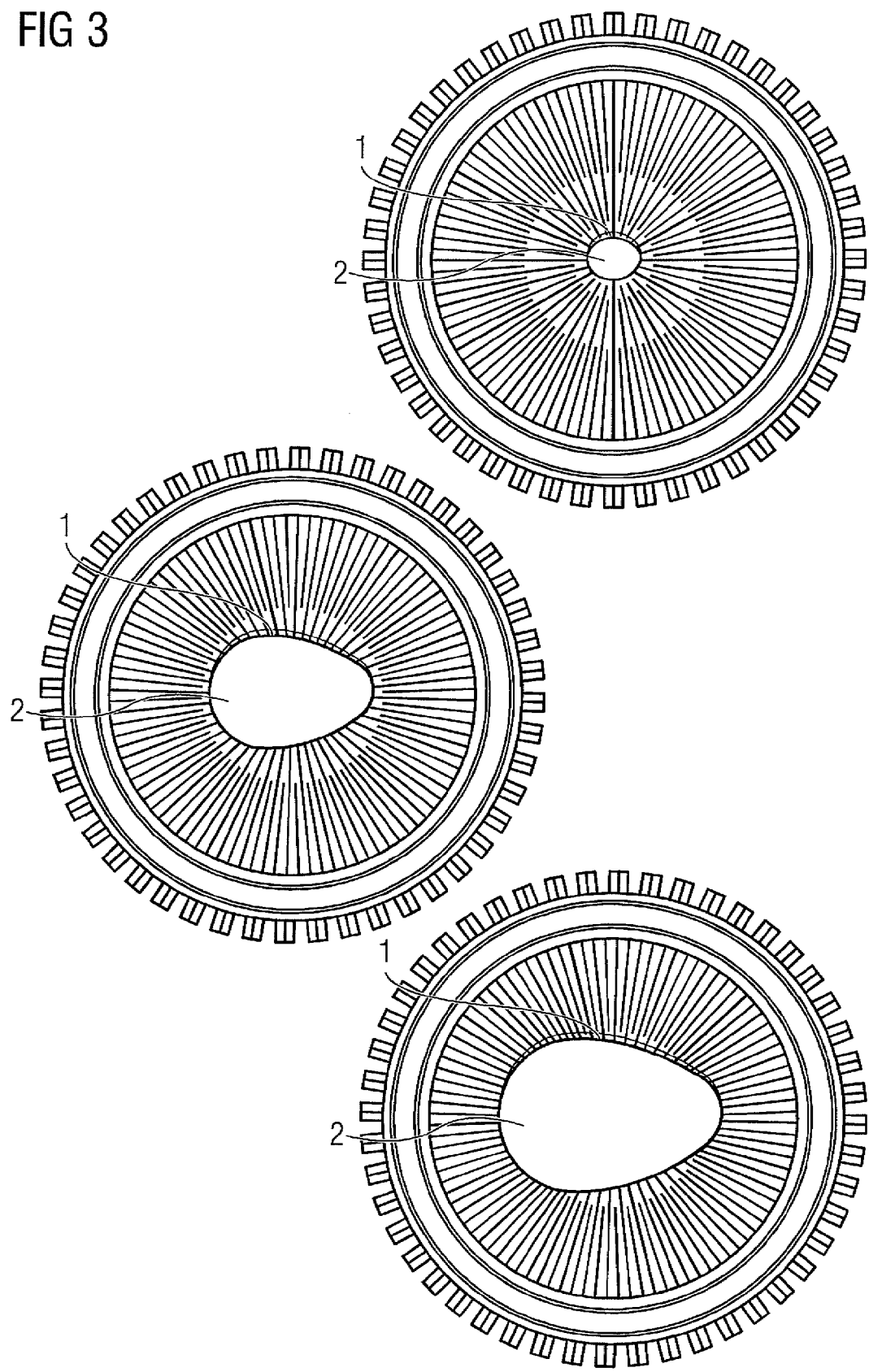
FIG. 3 shows a top view of embodiments of contour collimators having different contours.

FIG. 3 shows three top views of embodiments of contour collimators having different contours 1 and different apertures 2 thus generated, through which x-rays may reach a target volume.

FIG. 4 shows a spatial view of one embodiment of a contour collimator. The leaves 3 that form the chambers 4 are arranged in the housing 9. The pump units 6 are arranged on the exterior of the housing 9. The contour collimator rotates around the axis of rotation 8 in the direction of rotation R. By filling the chambers 4 with a liquid absorbing x-rays to a varying degree, different apertures may be generated for an irradiation.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A rotatable contour collimator for setting a contour of a radiation path of x-rays, the rotatable contour collimator forming an aperture and comprising:
    a liquid impermeable to x-rays in the rotatable contour collimator,
    wherein the contour is formed by forces affecting the liquid during rotation of the rotatable contour collimator.

2. The rotatable contour collimator as claimed in claim 1, wherein the liquid is arranged so as to be rotatable at right angles to the radiation path.

3. The rotatable contour collimator as claimed in claim 1, further comprising leaves arranged radially about an axis of rotation parallel to the radiation path.

4. The rotatable contour collimator as claimed in claim 3, wherein first ends of the leaves point in a direction of the axis of rotation, and
    wherein tapered chambers are formed between the leaves that are at least partially filled with the liquid.

5. The rotatable contour collimator as claimed in claim 4, further comprising pump units that exert the forces affecting the liquid in a direction of a centripetal force acting on the liquid.

6. The rotatable contour collimator as claimed in claim 5, wherein each of the pump units is operable to supply one of the tapered chambers.

7. The rotatable contour collimator as claimed in claim 1, wherein the liquid includes an euctectic alloy that contains gallium, indium and tin.

8. The rotatable contour collimator as claimed in claim 2, further comprising leaves arranged radially about an axis of rotation parallel to the radiation path.

9. The rotatable contour collimator as claimed in claim 1, further comprising pump units that exert the forces affecting the liquid in a direction of a centripetal force acting on the liquid.

10. The rotatable contour collimator as claimed in claim 2, further comprising pump units that exert the forces affecting the liquid in a direction of a centripetal force acting on the liquid.

11. The rotatable contour collimator as claimed in claim 3, further comprising pump units that exert the forces affecting the liquid in a direction of a centripetal force acting on the liquid.

12. The rotatable contour collimator as claimed in claim 2, wherein the liquid includes an euctectic alloy that contains gallium, indium and tin.

13. The rotatable contour collimator as claimed in claim 3, wherein the liquid includes an euctectic alloy that contains gallium, indium and tin.

14. The rotatable contour collimator as claimed in claim 4, wherein the liquid includes an euctectic alloy that contains gallium, indium and tin.

15. The rotatable contour collimator as claimed in claim 5, wherein the liquid includes an euctectic alloy that contains gallium, indium and tin.

16. The rotatable contour collimator as claimed in claim 6, wherein the liquid includes an euctectic alloy that contains gallium, indium and tin.

17. A method for setting a contour forming an aperture of a radiation path of an x-ray with a rotatable contour collimator, the method comprising:
    rotating the rotatable contour collimator, such that a force is applied to a liquid in the rotatable contour collimator, the liquid being impermeable to x-rays; and
    forming the contour by the force applied to the liquid during rotation of the rotatable contour collimator.

18. The method as claimed in claim 17, wherein rotating the rotatable contour collimator comprises rotating the rotatable contour collimator about an axis of rotation parallel to the radiation path.

19. The method as claimed in claim 18, wherein forming the contour comprises pumping the liquid in a direction of a centripetal force acting on the liquid.

* * * * *